United States Patent
Devine

(10) Patent No.: US 6,568,249 B2
(45) Date of Patent: May 27, 2003

(54) TEST METHOD AND APPARATUS FOR DETERMINING THE SURFACE SATURATED DRY CONDITION OF AGGREGATES

(75) Inventor: Patrick C. Devine, Columbus, OH (US)

(73) Assignee: Gilson Company, Inc., Lewis Center, OH (US)

(*) Notice: Subject to any disclaimer, the term of this patent is extended or adjusted under 35 U.S.C. 154(b) by 0 days.

(21) Appl. No.: 09/923,896

(22) Filed: Aug. 7, 2001

(65) Prior Publication Data

US 2003/0030450 A1 Feb. 13, 2003

(51) Int. Cl.[7] .................. G01N 5/02; F26B 21/08; F26B 11/02
(52) U.S. Cl. .................. 73/73; 73/76; 34/557; 34/595; 324/694
(58) Field of Search ............... 324/664, 694, 324/695, 703; 34/261, 534, 254, 550, 557, 595; 73/29.01, 73, 76

(56) References Cited

U.S. PATENT DOCUMENTS

| | | | |
|---|---|---|---|
| 4,738,034 A | * | 4/1988 | Muramatsu et al. .......... 34/524 |
| 5,050,528 A | * | 9/1991 | Yamada et al. .............. 118/19 |
| 5,212,453 A | | 5/1993 | Koehler et al. ............. 324/664 |
| 5,220,168 A | | 6/1993 | Adamski et al. ............. 250/339 |
| 5,397,994 A | | 3/1995 | Phare ........................ 324/688 |
| 5,651,194 A | * | 7/1997 | Hayashi ...................... 34/550 |
| 5,661,227 A | * | 8/1997 | Smith et al. ................. 324/694 |
| 5,784,801 A | * | 7/1998 | Thorp et al. ................. 34/115 |
| 6,393,725 B1 | * | 5/2002 | Smith et al. ................. 219/681 |

OTHER PUBLICATIONS

Title: Development of a New Test Method for Measuring Bulk Specific Gravity Of Fine Aggregates Date: Jan. 9, 2000. Authors: Prithvi S. Kandhal, Rajib B. Mallick, Mike Huner.

* cited by examiner

Primary Examiner—N. Le
Assistant Examiner—Anjan K. Deb
(74) Attorney, Agent, or Firm—David A. Greenlee

(57) ABSTRACT

A method and apparatus for determining the saturated, surface dry (SSD) condition point of aggregates includes warm air-drying of a water saturated aggregate sample of known initial weight. The sample is rotated in an open mesh screened drum, and heated ambient air is passed radially through the drum and the sample to remove water. Initially surface water is removed, followed by pore water. The loss in water weight and the exit air relative humidity (EAH) is tracked by sensors and recorded. The EAH values change significantly at the SSD point. Following SSD point determination, the test procedure continues until all free water is removed from the sample to determine total moisture content of the sample.

10 Claims, 5 Drawing Sheets

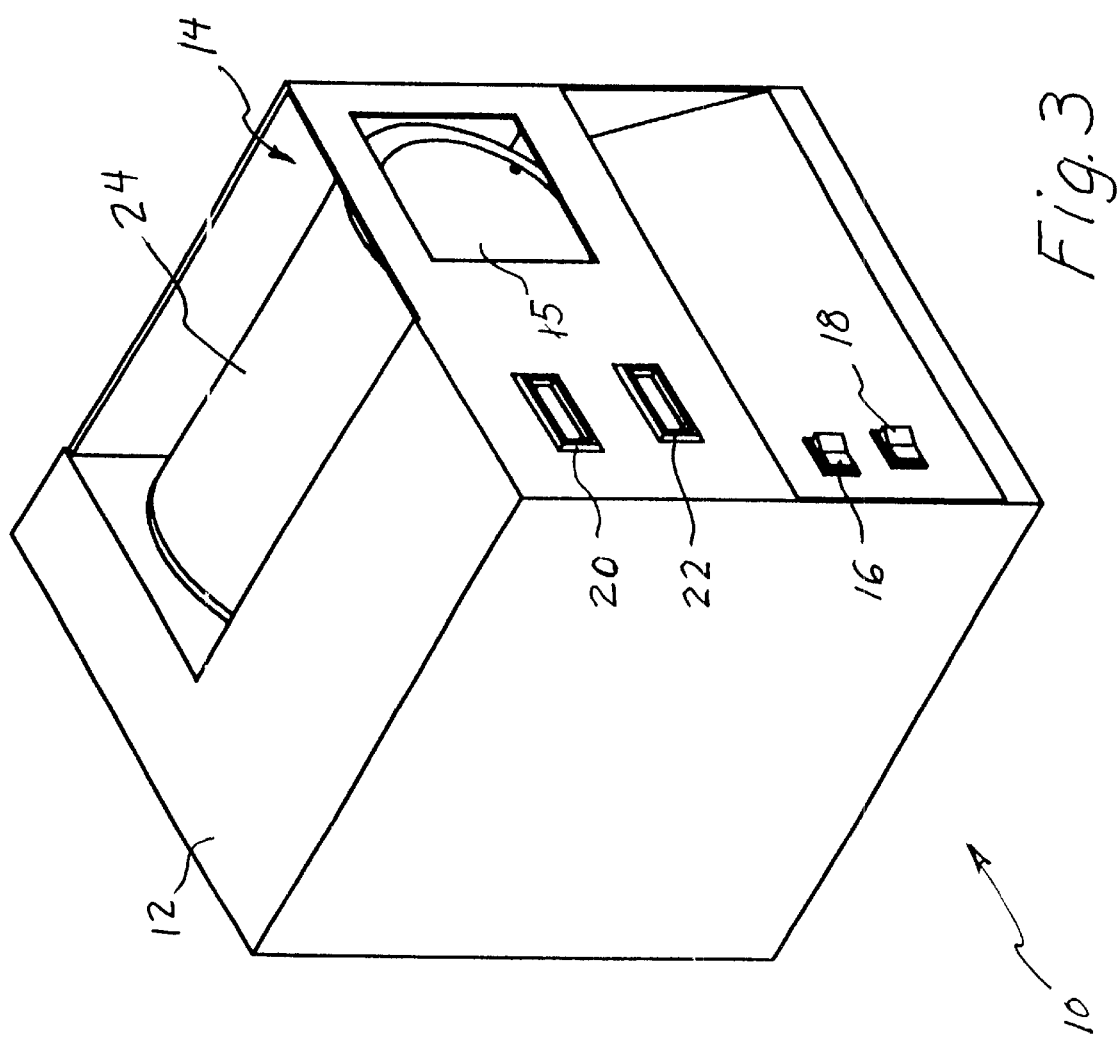

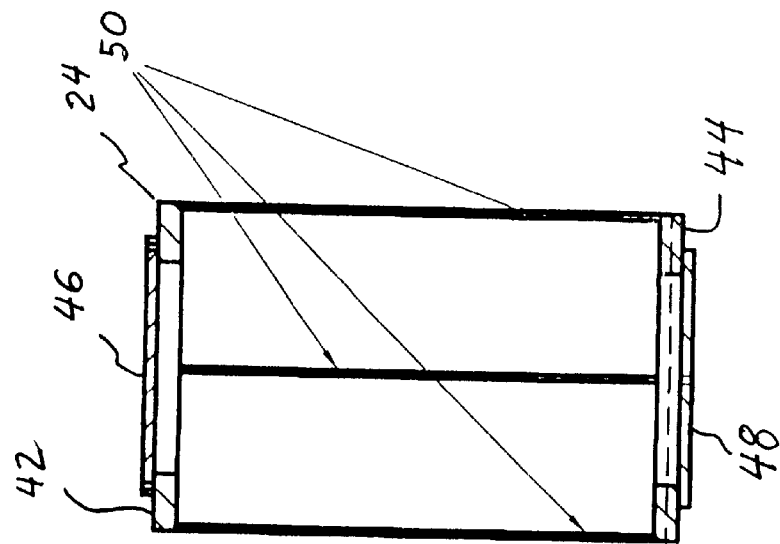
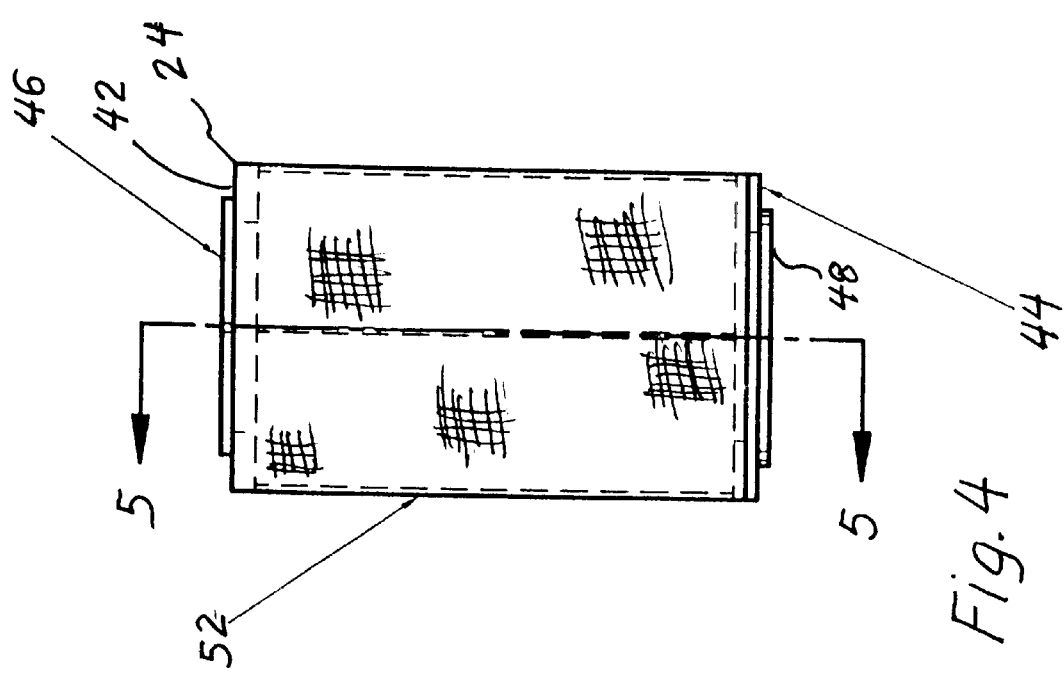

TEST METHOD AND APPARATUS FOR DETERMINING THE SURFACE SATURATED DRY CONDITION OF AGGREGATES

BACKGROUND OF THE INVENTION

Many industrial processes use or produce solids that contain water in various amounts and in various states of bonding. Bonding strengths of water range from waters of crystallization, to waters of hydration, to "free" water on the surface or in the pores of the material. Free water that is found on the surface or in the pore structure of many solids is bonded to the material by weak electrostatic forces. In contrast, waters of crystallization and hydration involve high energy ionic and covalent bonds, and the removal of such waters requires input energies beyond the scope of this invention.

The input heat energy required to break the bonding forces and remove the free water from the surface and pores of a material is generally less than required to break the covalent and ionic bonding forces of the waters of crystallization and hydration. This invention is directed to the removal of free water from porous materials such as aggregates, clays, minerals, cements, grouts, ceramic powders, and plastics.

Surface free water is water found on the surface of any material. A person touching or observing material having surface free water normally describes it as being "wet". When this surface water is removed, the material is normally described as being "dry". However, even so-called "dry" porous materials may contain substantial amounts of free water in their pore structure. Thus a material may have "pore water", independent of having any "surface water".

Surface water is bonded in a single plane—the surface, while small pore nacelles bind pore water in the multiple planes of the pore. Thus the pore water is slightly more strongly bonded than is the surface water, which requires less heat energy to evaporate than pore water. When a material is heated, the surface water evaporates first, followed by the pore water.

Fine aggregates (sand) are used in the manufacture of hot mix asphalt (HMA). To enable the asphalt binder to coat all surfaces of the aggregate particles, the particle must be free of surface water. Thus, it is important to determine when the aggregate is free of surface water. This is the point at which the aggregate reaches the saturated, surface dry (SSD) condition. It is important to know the bulk specific gravity of the fine aggregates in order to perform mix designs based on volumetrics. It is also important to know the amount of asphalt binder that can be absorbed by the aggregate and the percentage of voids in mineral aggregate (VMA). To calculate this, it is necessary to determine the moisture condition of the aggregate.

The current test methods to determine the SSD point of an aggregate sample are set forth in American Society of Testing Materials (ASTM) testing standard C128 and corresponding American Association of State Highway Transportation Officials (AASHTO) testing standard T84. The methods used in these tests are informally and collectively referred to as tamper and cone methods, in which an operator manually dries the sample with a hair dryer and then makes a cone pile of aggregate. This process is repeated until the cone slumps or collapses. The percent moisture of the sample at this point of collapse is recorded as the SSD point. Results of such tamper and cone tests vary widely from laboratory to laboratory, because the test is empirical, subjective and operator dependant.

Rounded natural sands produce useful SSD data under the current test protocols. However, the new Federal Highway Administration's SuperPave HMA mix design system favors the use of more angular manufactured aggregate sands. The current cone and tamper protocols do not produce useful SSD data for these angular manufactured fine aggregates, because the particles have a rough surface texture and the cones do not slump readily or reliably when the SSD point is reached.

Under a grant from the Federal Highway Administration, the National Center for Asphalt Technology (NCAT) devised a method to more accurately determine the SSD condition of manufactured fine aggregates. NCAT developed a device that is described in their paper "Development of a New Test Method For Measuring Bulk Specific Gravity of Fine Aggregates" by Kandhal et. al. given January 2000 at the Transportation Research Board $79^{th}$ Annual Meeting.

The NCAT device comprises a closed solid wall sample drum that has an air stream entrance opening at one end and a small air stream exit opening at its opposite end. After loading the drum with a precise sample amount of aggregate, the drum is rotated and warm air flows through the opening and axially through the sample, where it evaporates and absorbs the free water. The humidified air is forced out the exit, where its humidity is continually measured. The humidity changes when the SSD is reached and is recorded. A small circle of screen cloth is placed over the exit to prevent loss of sample aggregate in the exit air stream. Because of the small size of the exit opening, the screen cloth becomes easily clogged and requires frequent clearing. Recognizing the shortcomings of their test apparatus, NCAT issued invitations to instrument design companies to develop a commercially viable SSD instrument.

The equipment devised in response to this invitation generally involved known high tech principles of measuring sand moisture content and was expensive. Examples of equipment of this type can be found in U.S. Pat. Nos. 5,397,994—Phare (moisture probe using a resonant electric circuit connected to a diode detector), U.S. Pat. No. 5,220, 168—Adamski et al (utilizing measurement of light, having different wavelengths that are affected by moisture content, projected onto the surface of an aggregate sample), and U.S. Pat. No. 5,212,453—Koehler et al (measuring the dielectric constant of aggregate by measuring the time lapse of a pulsed signal through the aggregate, which is a function of moisture content). Equipment of these types is expensive and far more complex than the original simple NCAT equipment and would present a maintenance nightmare in the normal working environment of such testing equipment, which is in the field.

Thus, there is a need for a method and simple, reliable equipment for determining the SSD point of a fine aggregate sample, and for determining the moisture content of that sample.

SUMMARY OF THE INVENTION

It is therefore an object of this invention to provide a method and simple, reliable equipment for determining the SSD point of a fine aggregate sample, and for determining the moisture content of that sample.

This inventor recognized that, while the NCAT equipment is problematic, the operating principle, that exit air humidity readings noticeably change when the fine aggregate samples reach the SSD condition point, is sound and this point can be accurately determined.

This invention provides a testing device that includes a rotatable mesh drum for holding an aggregate sample. The drum is located in an enclosure that has an inlet for heated air and an outlet for humidified air. A fan supplies air that is heated by an electric heater and flows radially through the entire length of the rotating drum where it is humidified by water evaporated from the sample. This humidified air exits through the outlet where the temperature and humidity are continuously recorded. The rotation of the drum tumbles the aggregate sample. This, the use of mesh, and the radial airflow through the drum insure exposure of the entire sample to the heated air and prevent moisture pockets, which could produce false readings. The mesh drum also solves the clogging problem of the prior NCAT device.

The testing device is mounted on a scale to continuously monitor the weight change of the sample as moisture is evaporated out of the aggregate. A transparent window is provided in the housing to enable observation of the tumbling characteristics of the sample.

Periodic temperature and humidity readings are taken of the exit air to determine the SSD point. The drying of the sample is allowed to continue beyond the SSD point until weight readings show no more loss of free water. The final sample weight is recorded as totally dry weight. The total free water percent can then be calculated.

In one aspect, this invention features apparatus for determining the SSD point of an aggregate, comprising a sample drum for holding an aggregate sample having free water, said drum having spaced ends connected by a peripheral body that is sufficiently porous to allow air flow into and out of the drum, but contain the aggregate. A housing includes a closed chamber for the drum, an air inlet for allowing air to enter the chamber and flow radially through the drum, and an air outlet for enabling air within the drum to exit the chamber. The apparatus includes means for rotating the drum, means for heating inlet air and forcing the heated air into the chamber to evaporate and absorb the free water from the aggregate, and means for measuring the relative humidity of air exiting the chamber to enable determination of the SSD point of the sample.

Preferably, the drum body is made of a fine mesh, and the drum is supported by rollers In another aspect, this invention features a method of determining the SSD of an aggregate sample, comprising the steps of providing a sample drum having a peripheral body that is sufficiently porous to enable air flow through the drum, but contain the aggregate, placing the drum in a closed chamber, rotating the drum to tumble the aggregate, flowing heated air into and through the drum to humidify the air by evaporating and absorbing free water from the aggregate, exiting the moisturized air from the chamber, and measuring the relative humidity of the exit air to enable determination of the SSD point of the sample.

These and other features and objects will become more readily apparent upon reference to the following detailed description of a preferred embodiment of this invention, along with the drawings, in which:

BRIEF DESCRIPTION OF THE DRAWINGS

FIG. 3 is view similar to FIG. 1, but with the sample chamber door open;

FIG. 4 is a plan view of the sample drum;

FIG. 5 is a sectional view, taken along the line 5—5 of FIG. 4; and

DESCRIPTION OF THE PREFERRED EMBODIMENTS

Figure 1:
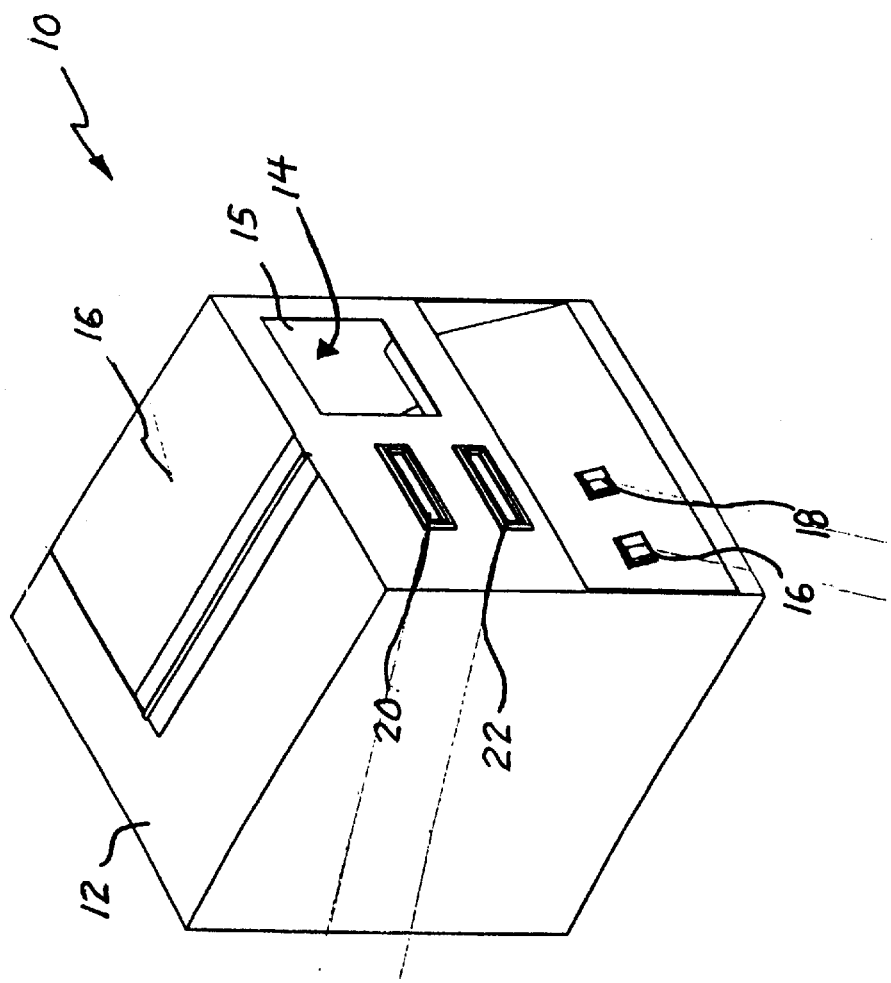
FIG. 1 is a perspective view of apparatus according to this invention, with the sample chamber in the closed position.

Referring to FIG. 1, the SSD test device 10 comprises a housing 12 having closed sample chamber 14, having a transparent window 15, that is accessible through an access door 16. The front panel of housing 12 mounts a main power switch 16, such as Eaton Model 2600HR11ECH, and a run/test switch 18, such as Eaton Model 2600HR11ECH). Also front-mounted are a relative humidity display 20, such as Digi-Key Model #227-1034-ND that displays the exit air humidity (EAH), and an input air temperature display 22, such as Digi-Key Model #227-1034-ND.

Figure 2:
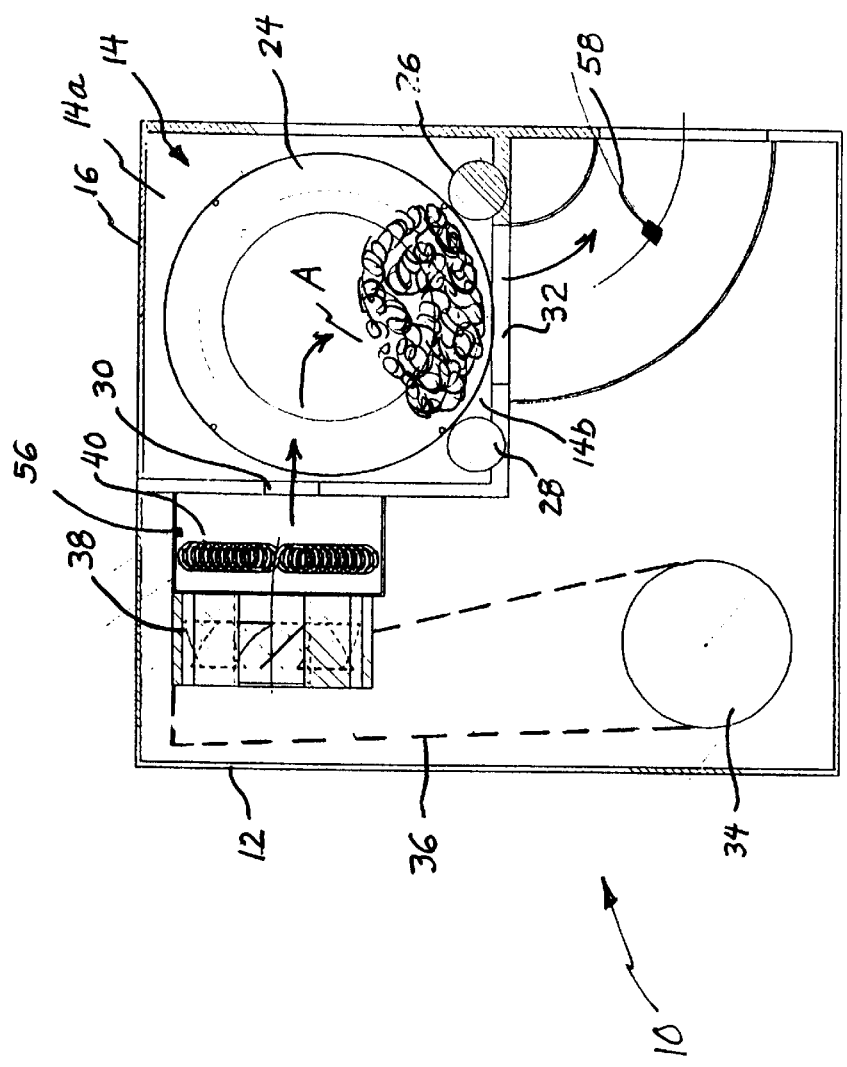
FIG. 2 is a sectional view of the apparatus of claim 1, showing the sample drum, blower, air ducts, heater, drive train, humidity and temperature sensors.

As shown in FIGS. 2 and 3, sample chamber 14 contains a sample drum 24 that is supported for rotation by a pair of spaced rollers 26 and 28. Chamber 14 has an air inlet 30 and an air outlet 32. Air is drawn into housing 12 through a port 34 and through ducting 36 by a blower 38, such as McMaster Carr Model #1976K43, and past a heater 40, such as McMaster Carr Model #20055K21, where it is heated before entering chamber 14 through inlet 30. Referring additionally to FIGS. 4 and 5, drum 24 comprises a pair of spaced acrylic end plates 42, 44 that have an access door 46 and an end plate 48, respectively, for placing sample aggregate "A" into, and removing it from, drum 24. Circumferentially-spaced stainless steel flights, or rods, 50 extend between end plates 42, 44 and are encased in a periphery of fine stainless steel mesh screen 52, such as US #200, to contain the sample aggregate A during testing.

Rollers 26 and 28 partially divide chamber into inlet portion 14a and outlet portion 14b and force most of the heated inlet air through the interior of drum 24 past the sample aggregate A. An temperature sensor 56, such as Extech Model #381277, monitors inlet air temperature for display on display 16, while a humidity sensor 58, such as Extech Model #445603, is located in the ducting beyond outlet 32 to monitor exit air humidity for display on display 18. A drive motor, such as Grainger Model #1L4A3 (not specifically illustrates) is mounted in housing 12 behind sample chamber 14 to rotate sample drum 24.

Figure 6:
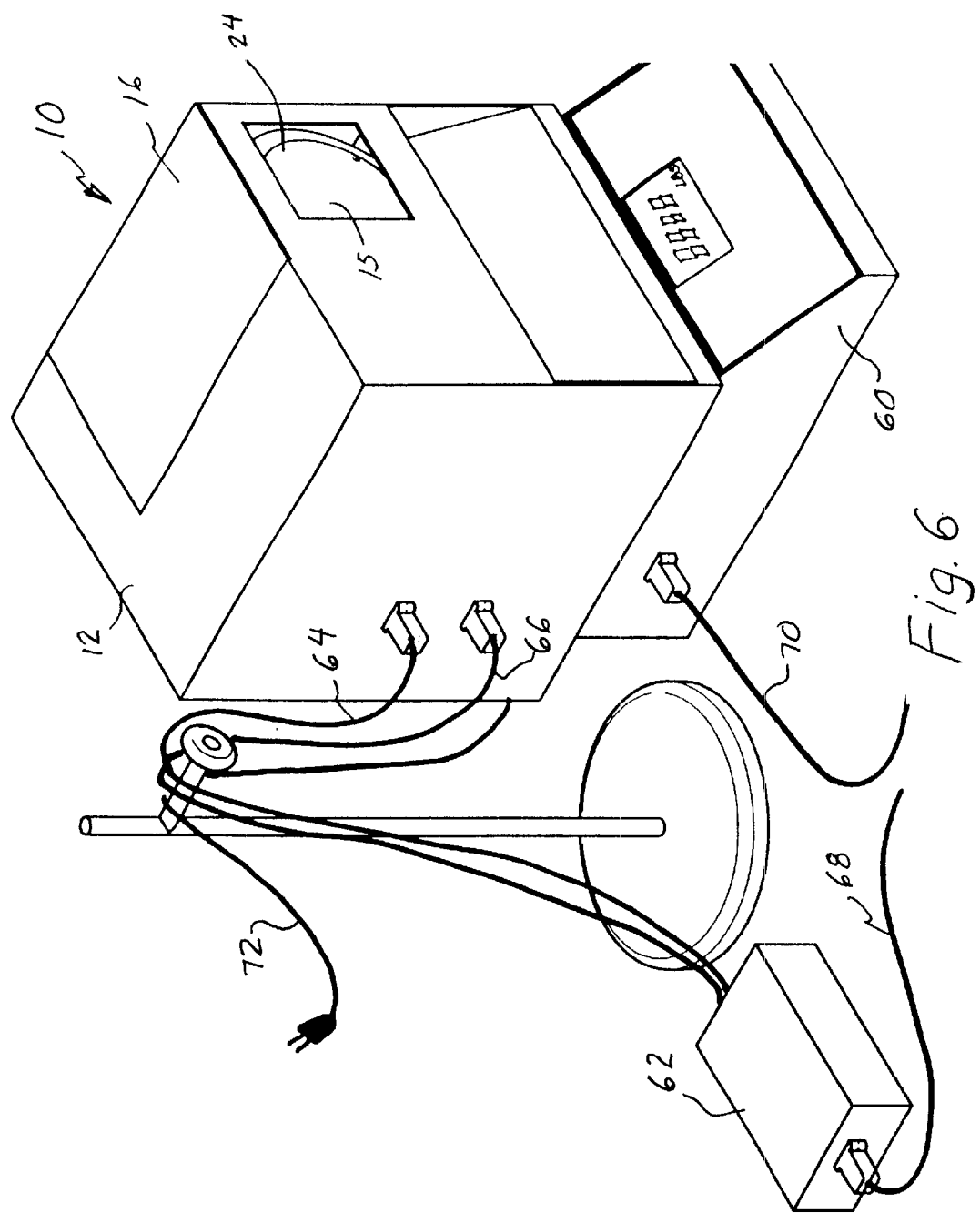
FIG. 6 is a perspective view of the apparatus shown mounted on a scale and with accessories enabling connection to a computer.

As shown in FIG. 6, the empty test device 10 is placed on an electronic scale or balance 60, such as Ohaus Model #EOM210 or A&D Model #HP-30K, to establish a tare weight. During testing, balance 60 tracks the loss in weight caused by evaporation of free water from the sample aggregate during the test period. As an alternate technique, the operator could tare and weigh only the sample drum to record all readings manually on any suitable weigh balance.

An analog-to-digital converter 62, such as IO Tec Model #DAK 55, is connected to test device 10 by temperature and humidity data lines 64, 66 and to a computer (not illustrated) by a line 68, while balance 60 has an output line 70 for connection to the computer. Test device 10 has the usual AC power cord 72.

Thus, testing device 10 includes rotatable mesh drum 24 for holding aggregate sample A in enclosure 14 that has inlet 30 for heated air and outlet 34 for humidified air. Fan 38 supplies air that is heated by heater 40, as monitored by sensor 56, and flows through the length of rotating drum 24 where it is humidified by free water evaporated from sample A. This humidified air exits through outlet 32 where the humidity is continuously monitored by sensor 58. The rotation of the drum tumbles the aggregate sample. This, the use of mesh, and radial airflow through the entire body of the drum insure exposure of the entire sample to the heated air and prevent moisture pockets, which could produce false readings. Testing device 10 is mounted on balance 60 to continuously monitor the weight change of the sample as moisture is evaporated out of the aggregate. Transparent window 15 is provided in housing 12 to enable observation of the tumbling characteristics of aggregate sample A.

Periodic temperature and humidity readings are taken of the exit air to determine the SSD point. The drying of the sample is allowed to continue beyond the SSD point until weight readings show no more loss of free water. The final sample weight is recorded as totally dry weight. The total free water percent can then be calculated.

In an example test procedure, approximately 1000 grams of water saturated fine aggregate is placed into sample drum 24, which has been pre-weighed. Data recorded by electronic balance 60 (weight), sensors 56 (temperature) and 58 (humidity) are continuously transmitted to a computer, which, with appropriate software, can calculate the SSD point and total sample moisture content. Of course, an operator could record all data manually from instrument and scale displays without necessitating use of a computer.

Closing sample drum lid, turning on blower, heater and sensors initiates the test. As test time progresses the operator or software records weight loss, EAH and input air temperature. EAH is plotted versus time and the SSD point is determined from the change in slope that occurs at SSD condition. A plot of sample weight versus time allows the percent moisture at SSD to be calculated.

The drying of the sample is allowed to continue beyond SSD condition until weight readings show no more loss of free water. The final sample weight is recorded as totally dry weight. The total free water percent can then be calculated.

While only a preferred embodiment has been shown and described, obvious modifications are contemplated within the scope of this invention, as defined by the following claims.

I claim:

1. Apparatus for determining the SSD point of an aggregate, comprising
    a sample drum for holding an aggregate sample having free water, said drum having spaced ends connected by a peripheral body that is sufficiently porous to allow air flow into and out of the drum, but contain the aggregate,
    a housing including a closed chamber for the drum, an air inlet for allowing air to enter the chamber and flow radially through the drum, and an air outlet for enabling air within the drum to exit the chamber,
    means for rotating the drum,
    means for heating inlet air and forcing the heated air into the chamber to evaporate and absorb the free water from the aggregate, and
    means for measuring the relative humidity of air exiting the chamber to enable determination of the SSD point of the sample.

2. The apparatus of claim 1, including means for periodically weighing the sample to determine loss of free water from the sample.

3. The apparatus of claim 2, wherein the weighing means mounts the housing to enable continuous weighing.

4. The apparatus of claim 1, including means for measuring the temperature of the inlet air.

5. The apparatus of claim 1, wherein the drum is cylindrical and the peripheral body is made of a fine mesh screen.

6. The apparatus of claim 1, wherein the housing includes a window enabling observation of the sample in the drum from outside the housing.

7. The apparatus of claim 6, wherein the housing includes an access door providing access to the chamber to remove and replace the drum.

8. The apparatus of claim 7, including a pair of rollers supporting the drum during rotation.

9. A method of determining the SSD of an aggregate sample, comprising the steps of
    providing a sample drum having a peripheral body that is sufficiently porous to enable air flow through the drum, but contain the aggregate,
    placing the drum in a closed chamber,
    rotating the drum to tumble the aggregate,
    flowing heated air radially through the drum to humidify the air by evaporating and absorbing free water from the aggregate,
    exiting the moisturized air from the chamber,
    measuring the relative humidity of the exit air to enable determination of the SSD point of the sample.

10. The method of claim 9, including the steps of
    continuously weighing the sample to enable determination of sample free water content, and
    measuring the temperature of the inlet air.

* * * * *